United States Patent [19]
Filley

[11] Patent Number: 5,554,126
[45] Date of Patent: Sep. 10, 1996

[54] MULTIPLE PURPOSE PROTECTIVE HYPODERMIC NEEDLE CAP

[76] Inventor: Daniel E. Filley, NE. 381 Bear Creek Dewatto Rd., Bremerton, Wash. 98312

[21] Appl. No.: 288,676

[22] Filed: Aug. 9, 1994

[51] Int. Cl.$^6$ .................................................. A61M 5/00
[52] U.S. Cl. ........................................ 604/192; 604/110
[58] Field of Search .............................. 604/110, 192, 604/198–263; 206/364–367

[56] References Cited

U.S. PATENT DOCUMENTS

| | | | |
|---|---|---|---|
| 3,021,942 | 2/1962 | Hamilton | 604/192 |
| 4,332,323 | 6/1982 | Reenstierna | 206/365 |
| 4,634,428 | 1/1987 | Cuu | 604/110 |
| 4,728,320 | 3/1988 | Chen | 604/110 |
| 4,846,808 | 7/1989 | Haber et al. | 604/195 |
| 4,950,242 | 8/1990 | Alvarez | 604/110 |
| 4,994,044 | 2/1991 | Lo Duca | 604/192 |
| 5,013,305 | 5/1991 | Opie et al. | 604/192 |
| 5,066,279 | 11/1991 | Russell | 604/110 |
| 5,078,694 | 1/1992 | Wallace | 604/192 |
| 5,084,027 | 1/1992 | Bernard | 604/192 |
| 5,088,985 | 2/1992 | Deras | 604/192 |
| 5,112,315 | 5/1992 | Gloyer et al. | 604/195 |
| 5,242,421 | 9/1993 | Chan | 604/198 |
| 5,347,078 | 9/1994 | Eckels | 588/258 |

Primary Examiner—John D. Yasko
Attorney, Agent, or Firm—Roy E. Mattern, Jr.

[57] ABSTRACT

A multiple purpose protective hypodermic needle cap which: is initially supplied by a manufacturer of a disposable hypodermic needle syringe: first, to protect the hypodermic needle during shipping and storing, until the syringe is ready for its medical use; second, after the syringe is utilized, the top of the cap, which has a preformed cavity, having a pocket depth serving as a gage, to receive and to position a predetermined length of the hypodermic needle, before it is bent, is positioned over the end portion of the hypodermic needle and then this cap is used as a tool to bend back this pointed, sharp end portion of the hypodermic needle beyond ninety degrees; third, the cap is moved clear of this bent end portion, then rotated and placed back over this bent end portion, and beyond; and fourth, the cap is moved over this bent end portion, until the pointed and sharp tip end of this bent end needle portion, radially expands, in a one way latching motion, into a receiving cavity, having an engagement lip to contact the pointed and sharp tip end if any removal is attempted. Both the cavity and engagement lip are initially formed and provided during the manufacture of this disposable hypodermic needle syringe. Thereafter, this utilized disposable hypodermic needle syringe is safely disposed of, because this multiple purpose protective hypodermic needle cap is locked on and cannot be removed, without completely destroying the needle and syringe.

17 Claims, 5 Drawing Sheets

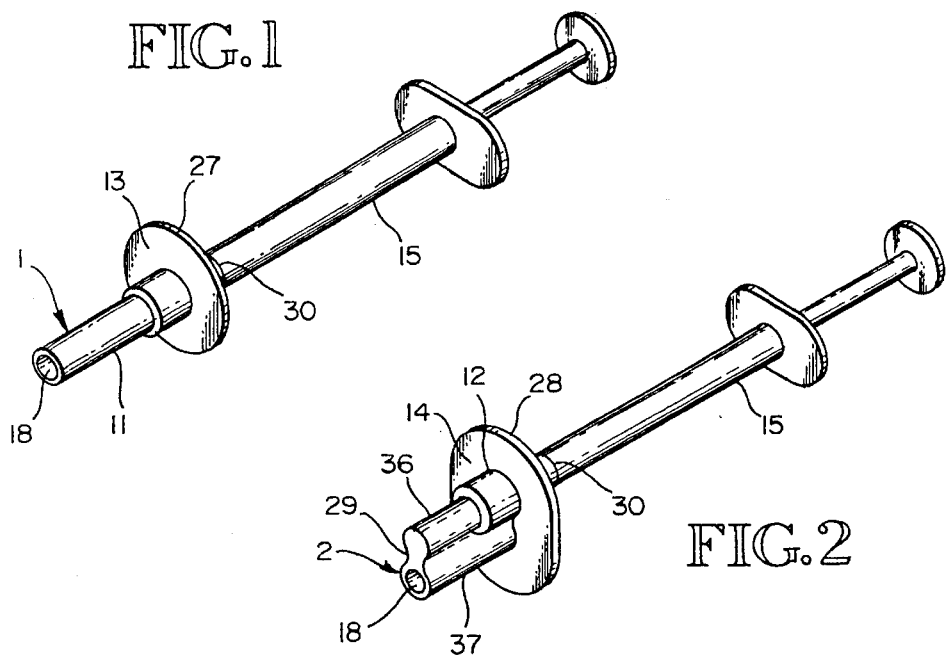
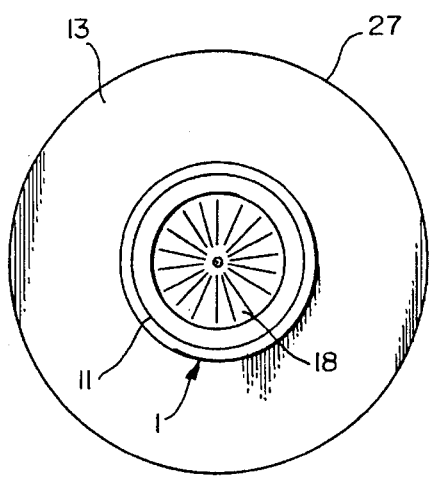
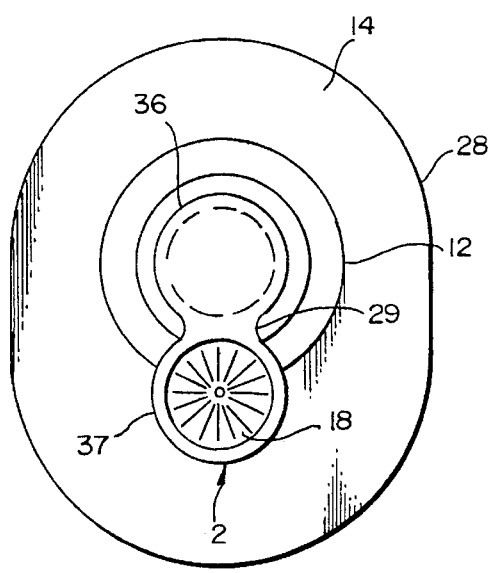

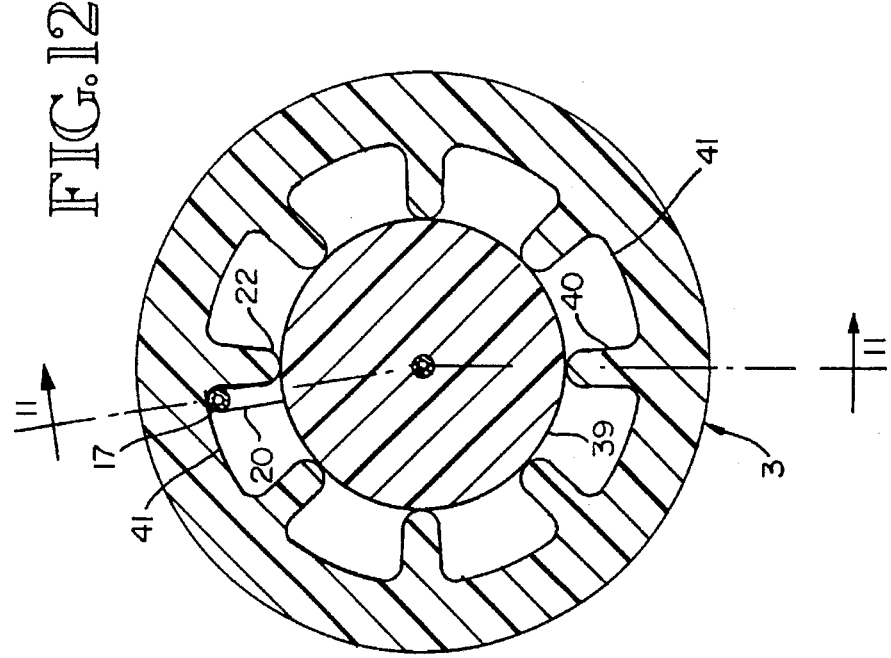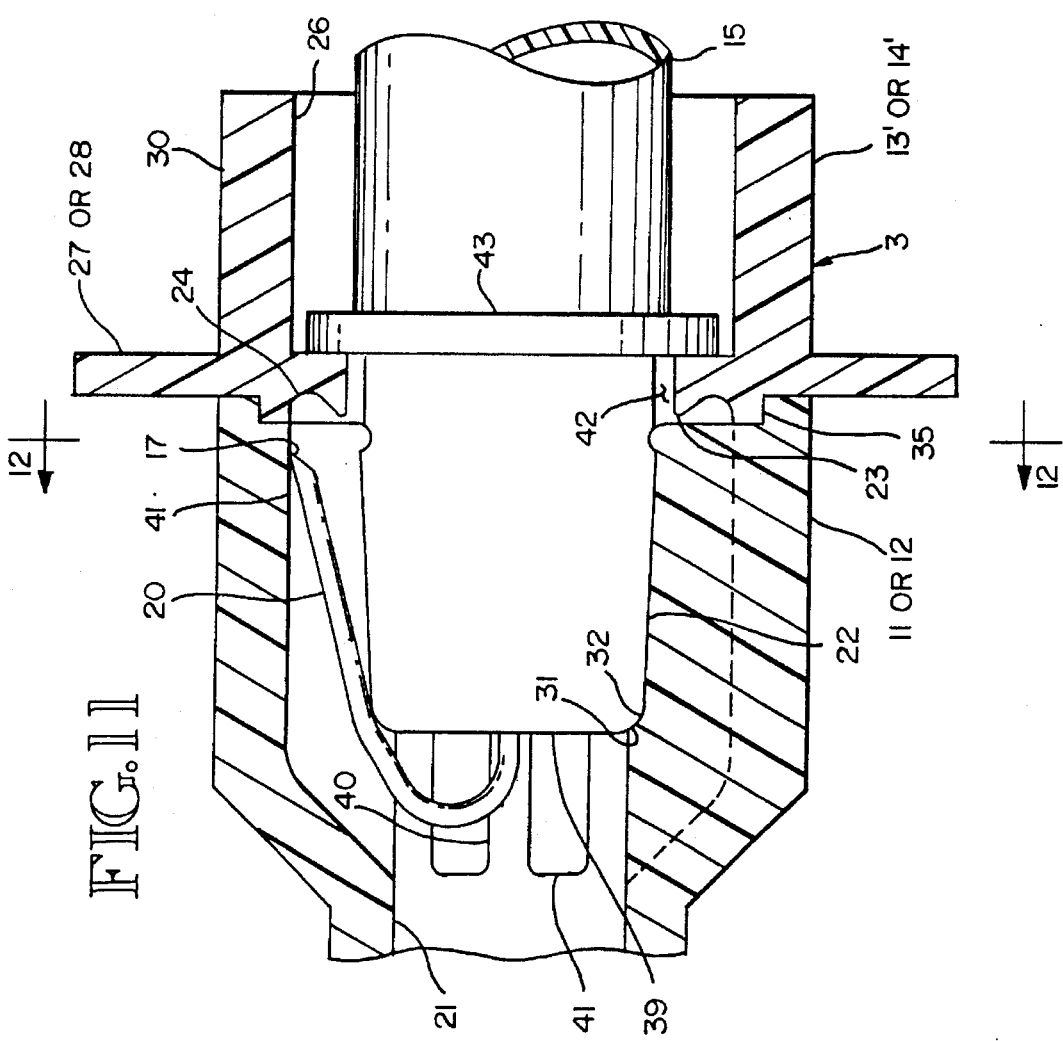

MULTIPLE PURPOSE PROTECTIVE HYPODERMIC NEEDLE CAP

BACKGROUND

Covers, i.e. caps, which at the outset, cover and protect hypodermic needles until the intentional use occurs of a disposable hypodermic needle syringe, and which, subsequently, cover the used hypodermic needle to protect persons from being pricked by a used hypodermic needle, have been, are, and will continue to be provided. As stated by Donald G. Russell in his U.S. Pat. No. 5,066,279 of Nov. 19, 1991 pertaining to his protective sheath for hypodermic needle:

"Incidences of injury and the spread of infection and contamination from inadvertent punctures or 'sticks' by hypodermic needles are a source of increasing concern in hospitals, physician's offices and other facilities which require medical personnel to handle and dispose of hypodermic needles after they have been used on a patient. Additionally, the appearance of medical waste and particularly 'sharps' such as hypodermic needles in areas not approved for disposal or, more importantly, public areas such as beaches and parks where disposal is not permitted, has lead to new environmental regulations governing the disposal of medical waste. The concern for infection of medical personnel and the spread of life-threatening diseases such as viral hepatitis and acquired immunity deficiency syndrome (AIDS) are forcing manufacturers of medical supplies to seek out new forms of protection and disposal to minimize the hazards arising from such waste.

Hypodermic needles pose a special hazard for medical personnel because they are used quite frequently, often in emergency situations where time is critical and care in handling is preempted by the exigencies of the situation. Additionally, hypodermic needles are generally supplied with a sheaf covering the needle and re-sheathing the needle after use poses a moderate risk of puncture since the sheath has a generally narrow opening and fingers holding the sheath are generally located immediately adjacent the opening. The problem with inadvertent punctures has lead some hospitals to establish regulations that prohibit medical personnel from re-sheathing needles after use. Of course, the consequence of such regulations is exposed, contaminated needles in the medical waste.

Still further problems that arise from hypodermic needles are the pilferage of medical waste by I.V. drug users and the infection that may arise from repeated use of the needles by different users. If the needles were decommissioned after use by authorized facilities, the spread of disease and contamination from pilfered hypodermic needles would be greatly reduced."

Mr. Russell, continuing in his background statement, refers to three U.S. Pat. Nos. 4,610,667; 4,740,204, and 4,799,927 disclosing:

"devices for destruction of a hypodermic needle after use. The earlier patent also mentions that a prior art technique for destroying a hypodermic needle includes bending the needle with a protective cap so that the needle can not be again re-used."

Thereafter Mr. Russell illustrates and describes his protective sheath for hypodermic needles to protect the needle until it is intentionally used. Then after the needle is used he describes his method of using his protective sheath to decommission this used needle so the needle cannot be used again, and the used needle remains covered during the intentional disposal of the used needle.

Donald Russell says:

"The sheath comprises a hollow tubular sleeve having a first longitudinal end with an opening for receiving a hypodermic needle. The tubular sleeve has a second longitudinal end opposite the first, and the length of the sleeve between the two ends is greater than the length of the needle to be encased by the sheath. The tubular sleeve also has a relatively rigid first tube section adjacent the first longitudinal end and a relatively rigid second tube section adjacent the second longitudinal end of the sleeve. An intermediate tube section joining the first and second tube sections is flexible to allow the first and second tube sections to be bent out of axial alignment with one another along with a hypodermic needle that is encased within the sheath. By bending the needle within the case, the needle is crimped and de-commissioned which prevents re-use, inadvertent or otherwise, and captures the needle within the sheath for safe disposal. The protective sheath therefore reduces possibilities of injury, infection and transmission of disease."

other patents, each of which refer to other references cited are:

In U.S. Pat. No. 4,332,323 of Jun. 1, 1982, Erik G. B. Reenstierna discloses his destruction device for injection needles, which is placed over a used hypodermic needle. Then during the application of a tapping force, the used needle is bent and/or broken, upon the relative motion of axial sleeves, which direct projections into destructive contact with the used needle. Thereafter, with the axial sleeves still in place, the entire disposable hypodermic needle syringe with this destruction device is safely disposed of.

In U.S. Pat. No. 4,634,428 of Jan. 6, 1987, Cwo-Liang Cuu illustrates and describes his cover for a disposable syringe. The cover is initially provided with the disposable syringe. Then after the intended use of the disposable syringe, the cover is manipulated to shorten its length so its self-contained bending and needle end retaining portion can receive, bend, and thereby restrain the needle, as this portion is rotated by using a tool, such as an Allen wrench.

In U.S. Pat. No. 4,728,320 of Mar. 1, 1988, Chang-Cheng Chen disclosed his syringe cap with a hammer. His abstract reads as follows:

"A syringe cap includes a hollow cap body and a hammer body fitted in a fitting body which in turn is fitted slidably in an end of the cap body for telescoping movement. The hammer body has a hitting end with a concave surface facing a closed end of the fitting body which can be pierced by the needle. The needle bent by the concave surface can engage permanently with the closed end so that the hammer body and the fitting body will never separate from the cap body."

In U.S. Pat. No. 4,846,808 of Jul. 11, 1989, Messrs. Haber and Foster illustrated and described their safety syringe having a needle to be retracted and canted within a protective sleeve. Their abstract reads:

"A shielded safety syringe comprising a cylindrical outer protective sleeve, a cylindrical inner needle carrier movable axially through the outer sleeve, and a double-ended hypodermic needle retained at a distal end of the needle carrier and movable with the carrier through the sleeve. A movement of the inner needle carrier through the outer protective sleeve corresponding causes the needle to be relocated from an axially extended position, at which to make a veni puncture through a patient's tissue, to a retracted position, at which the needle is completely surrounded and shielded by the outer sleeve to permit a safe handling and disposal of the syringe. A portion of the distal end of the needle carrier at which the needle is retained is pivotally connected to the needle carrier. When the needle is located in the retracted position, said distal end portion may be rotated and the needle thereby canted toward the outer sleeve to prevent both access to the needle and the return of the needle to the axially extended position, whereby to avoid an accidental needle strike and the spread of a contagious and, possibly life threatening, disease."

In U.S. Pat. No. 4,994,044 of Feb. 19, 1991, Carmelo Lo Duca discloses his protective needle syringe. He provides a syringe comprising:

"a needle having, at its end opposite to its tip, a collar with a frustum of cone shaped outer surface, a cap being provided to protect the needle after use, said cap having a cavity in which the needle can be completely inserted and protected, said cavity being open at one of its ends where a seat that is substantially complementary to that of the needle collar is formed, characterized in that the cap, close to its open end, is provided with elastically deformable catching members, said members strongly engaging the collar of the needle when the needle is forced and completely pushed into the cap cavity."

All of these previous ways of first protecting the hypodermic needle of a disposable hypodermic needle syringe to keep it medically ready for patient use, and thereafter to keep it from injuring anyone, and often to destroy it, preventing its reuse are acknowledged and respected. Yet there remains a need for a relatively low cost, conveniently manufactured, easy to use, multiple purpose hypodermic needle cap to be provided initially with a disposable hypodermic needle syringe, and which is subsequently used to bend and to fully capture and lockingly surround the used and then destroyed hypodermic needle.

SUMMARY

A multiple purpose hypodermic needle cap assembly is made available to be initially provided with a disposable hypodermic needle syringe to protect this needle until the syringe is intentionally used in the care of a patient. After the syringe is used, this multiple purpose hypodermic needle cap assembly is used first as a tool to bend the end portion of the needle and thereafter, as a cap assembly, to capture this bent end portion within the interior thereof, locking this cap assembly on the syringe. Subsequently, the syringe and the locked on cap assembly covering the bent, i.e. destroyed, hypodermic needle, is ready for safe disposal.

In one embodiment, the multiple purpose hypodermic needle cap assembly is initially manufactured in two parts, each of which is produced by the injection molding of plastic. Thereafter, during the overall manufacturing process, these two parts are axially aligned and secured together by optionally using either a heatstake, ultrasonic weld, or adhesive process.

The first part, referred to as the cap, resembles the standard cap, but is longer, to include a conical shaped cavity structure, serving as a needle bend gage, which subsequently is placed over the end portion of a used needle during the destructive bending of this end portion of the needle. This conical shaped cavity structure, also referred to as a needle bend gage cavity, has a pocket depth, serving as the gage, to receive and to position a predetermined length of the hypodermic needle, before the needle is bent, when later the cap is used as a tool to bend the needle end. Then this first part has an integral central portion, which is adjacent to the conical shaped cavity structure, and it has an interior hollow cylindrical structure to adequately receive a new needle and also portions of the body of the syringe. Then this first part, serving as a cap, has an integral ending portion having an outer receiving shoulder structure used in securing the two parts together, and an inner flared cavity structure to later receive the pointed end of the bent needle end.

The other part, i.e. the second part, of these two parts, referred to as the cover, has an interior complementary inner receiving shoulder structure for snugly overlapping the inner receiving shoulder structure of the first part, serving as the cap. The interior of this second part, serving as the cover, also has a syringe surrounding receiving chamber structure formed with both a receiving cavity structure and an engagement circular lip structure, which together subsequently receive and capture the pointed tip of the bent needle end, to in turn hold the entire cap assembly in place over the bent needle during the disposal of the used syringe. The follow on integral portions of this second part, serving as the cover, snugly surround the syringe.

Optionally this second part, i.e. There cover, is formed to include a surrounding finger guard flange. When a person is directing the multiple purpose hypodermic needle cap over the pointed tip of a used needle, this finger guard flange insures the protection of the person's fingers, as he or she is bending the end of the needle into its non-use destroyed position. Later, when this multiple purpose hypodermic needle cap assembly is directed over the bent used needle end, this finger guard flange again serves to protect the fingers of the person, as he or she is moving this multiple purpose hypodermic needle cap assembly over the entire bent needle. At the completion of this protective capping movement, the pointed tip of the bent portion of the needle enters the syringe surrounding chamber structure and is guided into the receiving cavity structure and held by the engagement circular lip structure of this cover part, in a one way latching sequence or motion. The used syringe is then ready for safe disposal.

Also optionally this second part, serving as the cover, is formed to have an extended finger grip portion, with or without the addition of the optional surrounding finger guard flange.

In another embodiment, which is shorter, the first part of this embodiment, also called the cap, has a figure eight cross-sectional shape providing along a principal axis a cylindrical-like body portion with an interior hollow cylindrical structure to adequately receive a new needle and also portions of the body of the syringe. Then this hollow portion of the cap in this first cylindrical-like body portion of the figure eight cross-sectional shape has an interior hollow flaring portion, forming a flared cavity, making a larger entry to the interior hollow cylindrical structure. This flared cavity later receives the bent end of the hypodermic needle.

Then another cylindrical-like body portion of the figure eight cross-sectional shape, located adjacent and parallel to the other cylindrical-like body of the figure eight cross-sectional shape, commences with a conical shaped cavity structure, serving as a needle bend gage, which subsequently is placed over the end portion of a used needle, when the cap assembly is used as a tool, during the destructive bending of this end portion of the hypodermic needle. This conical shaped cavity structure, also referred to as a needle bend gage cavity, has a pocket depth, serving as the gage, to receive and to position a predetermined length of the hypodermic needle, before the needle is bent, when later the cap assembly is used as a tool to bend the needle end. In line, beyond the conical shaped cavity structure, there is a hollow cylindrical structure formed to align the cover and to save plastic molding material and to keep the overall structure of this first part of this shorter embodiment, both strong and easy to handle.

The second part, also called the cover, of this shorter embodiment snugly overlaps the cylindrical-like body portion of the cap, i.e. the first part, where the hollow flaring portion is located. The interior of this cover part has a syringe surrounding receiving chamber structure formed with a receiving cavity and an engagement circular lip structure, which together subsequently receive and capture the pointed tip of the bent needle end, to in turn hold the entire cap assembly in place over the bent needle during the disposal of the used syringe. The follow on integral portions of this cover fit snugly surround the syringe. Optionally this cover is extended to provide a finger grip portion.

also optionally, this second part, serving as the cover, is formed to include a surrounding finger guard flange. When a person is directing this shorter embodiment of the multiple purpose protective hypodermic needle cap assembly as a tool over the end of a used needle, this finger guard flange insures the protection of the person's fingers, as he or she is using the cap assembly as a gage and as a tool to bend the end of the needle into its non-use destroyed position. Then later, when this shorter embodiment of the multiple purpose protective hypodermic needle cap assembly is directed over the bent used needle end, this finger guard flange again serves to protect the fingers of the person, as he or she is moving this multiple purpose protective hypodermic needle cap assembly over the entire bent needle. At the completion of this protective capping movement, the tip of the bent portion of the needle enters the syringe surrounding receiving chamber structure, and is guided for entry into the receiving flared cavity, and then is held, upon a one way latch action, by the engagement circular lip structure of this cover, i.e. second part. The used syringe is then ready for safe disposal.

DRAWINGS OF THE PREFERRED EMBODIMENTS

The multiple purpose protective hypodermic needle cap assembly is illustrated in the drawings in respect to preferred embodiments, with one embodiment being longer than another embodiment, and another embodiment showing how the embodiments are changed when used with two piece syringes which are designed to accommodate interchangeable needles.

FIG. 1 is a perspective view of the longer embodiment, referred to as the long cap assembly, in place on a ready to use disposable hypodermic needle syringe, showing an optional finger guard flange and a finger grip portion;

FIG. 2 is a perspective view of the shorter embodiment, referred to as the short cap assembly, in place on a ready to use disposable hypodermic needle syringe, showing the optional finger guard flange and finger grip portion;

FIG. 3 is a front end view of the longer embodiment;

FIG. 4 is a front end view of the shorter embodiment;

Figure 5:
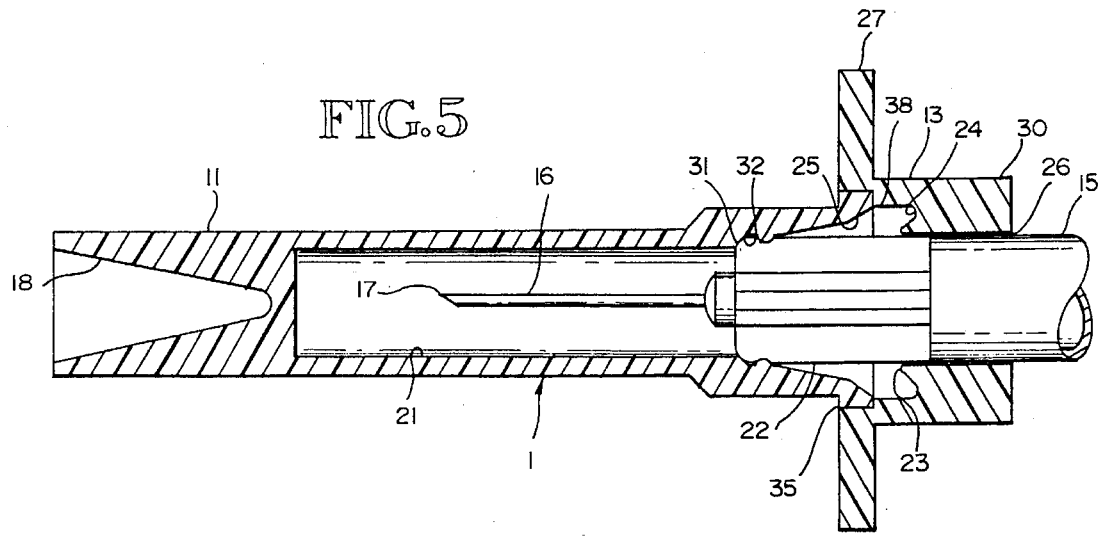
FIG. 5 is a partial cross-sectional view of the longer embodiment in place on a ready to use disposable hypodermic needle syringe, showing, however, only a limited portion of the syringe.
Figure 7:
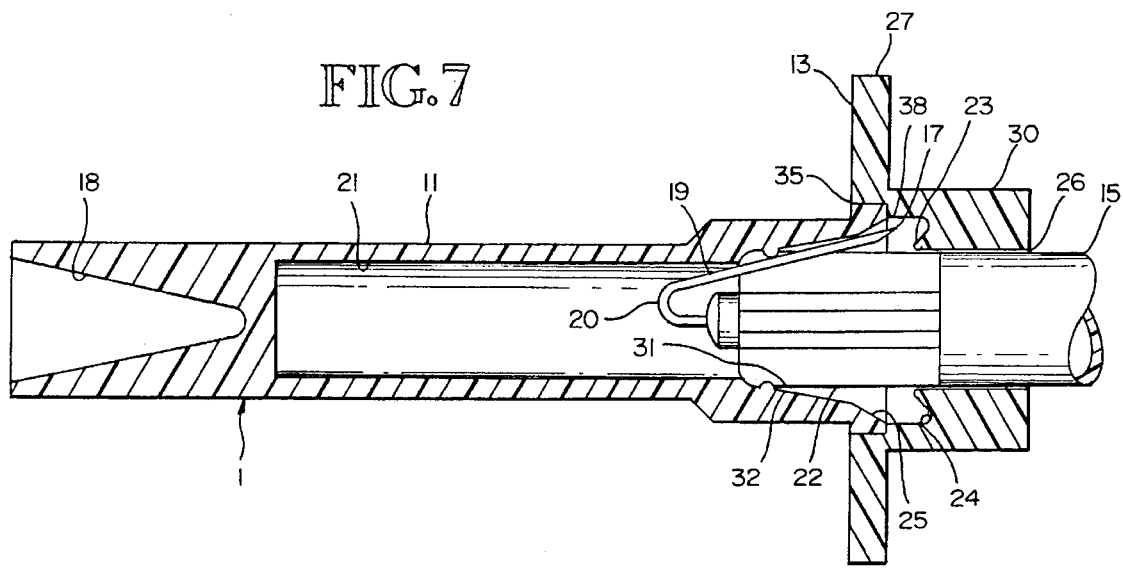
Figure 8:
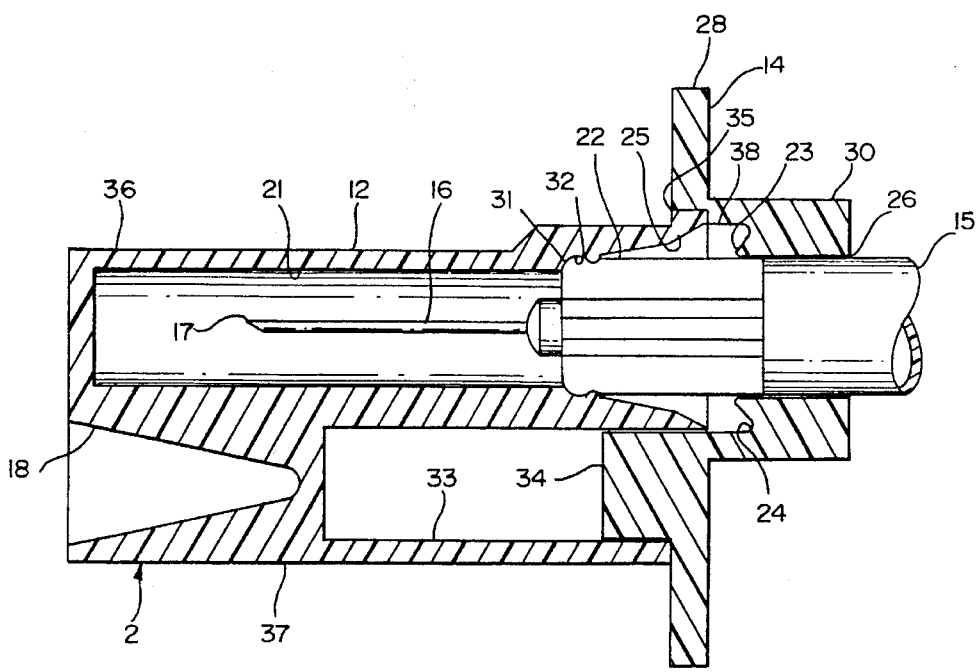
Figure 9:
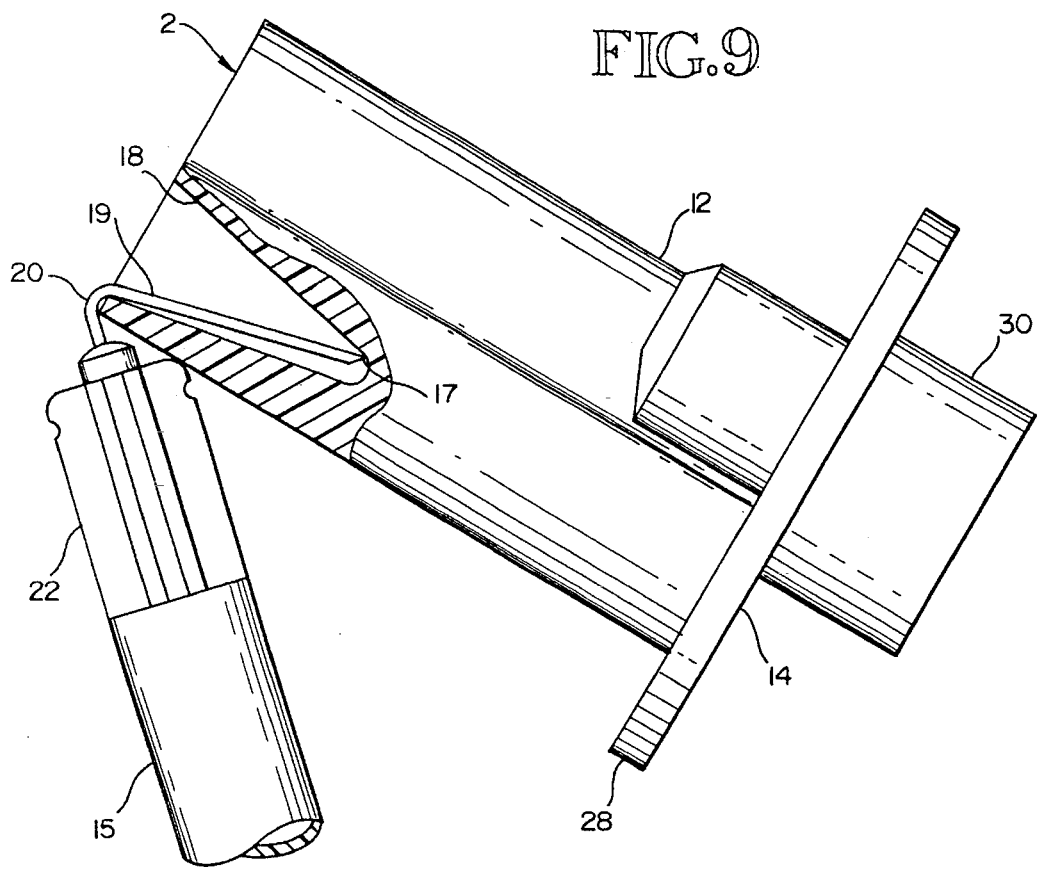
Figure 10:
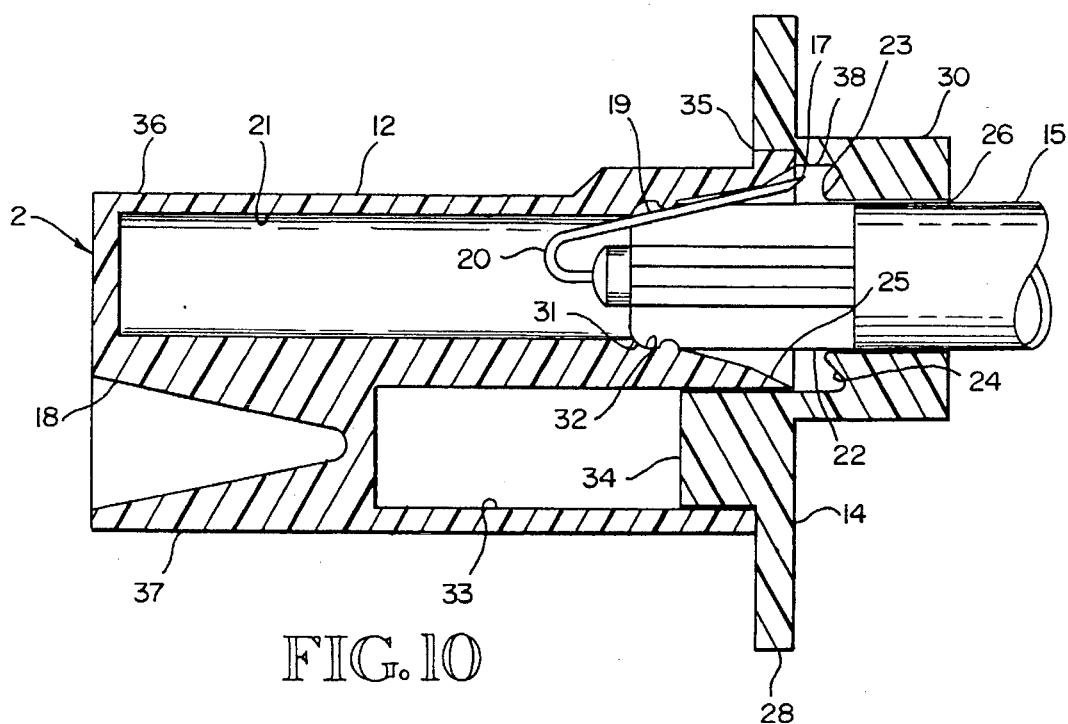

FIG. 7 is a partial cross-sectional view, similar to FIG. 5, showing the longer embodiment, which has been placed back over the bent hypodermic needle and locked into place in a one way latching action, so the used disposable hypodermic needle syringe can be safely disposed of, with the needle, in its destroyed configuration, being fully covered by this multiple purpose protective hypodermic needle cap assembly, which cannot be removed without fully destroying the needle;

FIG. 8 is a partial cross-sectional view of the shorter embodiment in place on a ready to use disposable hypodermic needle syringe, showing, however, only a limited portion of the syringe;

FIG. 9 is a partial cross-sectional view of the shorter embodiment which has been removed, and it is being used as a gage and a tool to bend the end portion of the used hypodermic needle to at least ninety degrees;

FIG. 10 is a partial cross-sectional view, similar to FIG. 8, showing the shorter embodiment, which has been placed back over the bent hypodermic needle and locked into place in a one way latching action, so the used disposable hypodermic needle syringe can be safely disposed of with the needle, in its destroyed configuration, being fully covered by this multiple purpose protective hypodermic needle cap assembly, which cannot be removed without fully destroying the needle and/or the syringe; and FIG. 11 is a partial cross-sectional view of resulting additional embodiments based upon either the long or short embodiments, which are, in effect, changed to accommodate two piece syringes, which in turn have interchangeable needles; and FIG. 12 is a sectional view taken along line 12—12 of FIG. 11, and in this FIG. 12, line 11—11 indicates where the partial cross-sectional view of FIG. 11 was taken in respect to this embodiment of the multiple purpose protective hypodermic needle cap assembly showing the internal grooved cap.

DESCRIPTION OF THE PREFERRED EMBODIMENTS

Introduction

The various multiple purpose protective hypodermic needle cap assemblies are illustrated in the drawings in respect to preferred embodiments. One embodiment 1, referred to as the long cap assembly 1, is longer than another shorter embodiment 2, referred to as the short cap assembly 2. Then a third illustrated embodiment 3, called the internal grooved cap assembly 3, indicates how embodiments 1 and 2 can be modified to cover two piece syringes, which have interchangeable needles. In respect to each embodiment and others not illustrated, the multiple purpose protective hypodermic needle cap assembly, is initially supplied by a manufacturer of a disposable hypodermic needle syringe 15.

First these protective cap assemblies 1, 2, and 3 protect the hypodermic needle 16, which is not visible during shipping and storing, until the syringe 15 is ready for its medical use, as illustrated in FIGS. 1, 2, 5 and 8.

Figure 6:
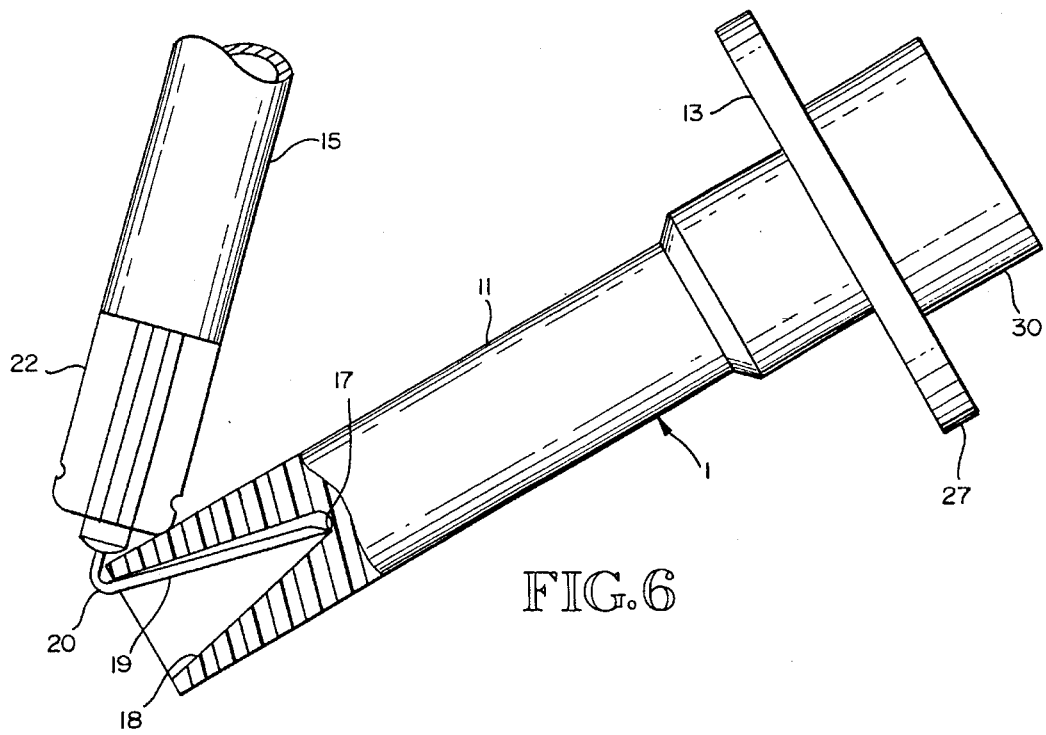
FIG. 6 is a partial cross-sectional view of the longer embodiment which has been removed, and it is being used as a gage and a tool, to bend the end portion of the used hypodermic needle to at least ninety degrees.

Second, after the syringe 15 has been utilized, these protective cap assemblies are used as a gage and tool as shown in FIGS. 6 and 9. The closed ends of the three illustrated cap assemblies 1, 2, and 3, all have a preformed cavity 18, preferably a conical cavity 18, which is positioned over the sharp end 17 of the hypodermic needle 16. This conical shaped cavity 18, also referred to as a needle bend gage cavity 18, has a pocket depth, serving as a gage, to receive and to position a predetermined length 19 of the hypodermic needle 16 before the needle 16 is bent.

Third, the protective cap assemblies are used as a tool to bend the predetermined length 19 of the hypodermic needle 16 at least ninety degrees, as shown in FIGS. 6 and 9.

Fourth, the protective cap assemblies 1, 2, or 3, are moved clear of the bent needle 20 having a predetermined needle bend length 19, and then turned end for end.

Fifth, the protective cap assemblies are then moved over and beyond the bent needle 20, as the needle is again pushed through a respective entrance bore 26 of a respective cover 13 or 14, as modified 13' or 14', when two piece syringes with interchangeable needles 16 are covered. Thereafter the bent needle 20 is fully received within the needle protective cavity 21, also referred to as the interior hollow cylindrical structure 21, of a respective protective cap assembly 1, 2, or 3, which initially fully received the new needle 16 and also the needle supporting structure 22 of the syringe 15 as shown in FIGS. 7, 10, and 11. At the completion of this replacement of these respective multiple purpose protective hypodermic needle cap assemblies 1, 2, or 3, the sharp end 17 of the bent needle 20 is moved through a one way latching motion, which results in locking these hypodermic needle cap assemblies in place over the entire bent needle 20 and also over the needle support structure 22 of the syringe 15, as shown in FIGS. 7, 10, and 11. Any forced attempt to remove these multiple purpose protective hypodermic needle cap assemblies 1, 2, or 3, from a syringe 15, completely destroys the bent needle 20 and/or the syringe 15.

The Longer Embodiment of the Multiple Purpose Protective Hypodermic Needle Cap.

The longer embodiment 1 of these multiple purpose protective hypodermic needle cap assemblies 1, 2, or 3, as illustrated in FIGS. 1, 3, 5, 6 and 7, is initially manufactured in two parts, the long cap 11 and long cover 13, each of which is preferably produced by the injection molding of plastic. Thereafter, during the overall manufacturing process, these two parts are axially aligned along a common centerline and secured together by optionally using either a heatstake, ultrasonic weld, or adhesive process.

The first part, referred to as the long cap 11, resembles a standard protective cap, but it is longer, having a closed end, to include a conical shaped cavity 18, having a predetermined pocket depth and serving as a needle bend gage, which subsequently is placed over the then predetermined length 19 of the sharp end 17 of the needle 16, of the syringe 15, during the destructive bending of this sharp end 17 of the needle 16.

Then this long cap 11 has an integral central portion, which is adjacent to the conical shaped cavity 18. It has an interior hollow cylindrical structure, referred to as the receiving cavity 25, which adequately receives both a new needle 16 and a needle supporting structure 22 of the body of the syringe 15.

Thereafter, this long cap 11, as the first part, has an integral ending shoulder structure, having, in turn, both an outer receiving shoulder 35, used in securing the two parts together, and an inner flared receiving cavity 25 to later receive the bent needle 20.

The other part, i.e. the second part, called the long cover 13, of these two parts 11 and 13, of this longer embodiment 1, has an interior complementary inner receiving shoulder structure, also designated by numeral 35, to indicate mating surfaces, for snugly overlapping the outer receiving shoulder 35 of the first part 11. The interior of this second part 13, also has a syringe surrounding receiving chamber 38 formed with both a receiving flared cavity 25, and an engagement circular locking ring-lip 23, which together subsequently receive and capture the sharp end 17 of the bent needle 20, to in turn hold the entire multiple purpose protective hypodermic needle cap assembly 1, of this embodiment in place over the bent needle 20 during the disposal of the used syringe 15. The follow-on integral portions of this second part, referred to as the long cover 13, snugly surround the syringe 15.

As shown in FIGS. 1, 3, 5, 6, and 7, this long cover 13 is formed to include a surrounding finger guard flange 27. When a person is directing this multiple purpose protective hypodermic needle cap assembly 1, in this longer embodiment, over the sharp end 17 of a used needle 16, this finger guard flange 27 insures the protection of the person's fingers, as he or she is bending the end of the needle 16 into its non-use destroyed position. Subsequently, when this multiple purpose protective hypodermic needle cap assembly 1 is directed over the used bent needle 20, this finger guard flange 27 again serves to protect the fingers of the person, as he or she is moving this multiple purpose protective hypodermic needle cap assembly over the entire bent needle 20.

At the completion of this protective capping movement, the sharp end 17 of the bent needle 20, enters the syringe surrounding receiving chamber 38 of the long cover 13 and is guided into the receiving flared cavity 25 of the long cap 11, and then the bent predetermined needle bend length 19, springs radially outwardly past the locking ring-lip 23, causing the sharp end 17 of the bent needle 20 to be held by engagement into the locking ring groove 24 of this long cover 13, in a one way latching sequence or motion.

Also, optionally, this second part, referred to as the long cover 13, is formed to have an extended finger grip 30, with or without the addition of the optional surrounding finger guard flange 27, as shown in FIGS. 1, 3, 5, 6, and 7.

The Shorter embodiment of the Multiple Purpose Protective Hypodermic Needle Cap

In another embodiment, called the short cap assembly 2, of these multiple purpose protective hypodermic needle cap assemblies is illustrated in FIGS. 2, 4, 8, 9 and 10. The first part 12 of this embodiment 2 is called the short cap 12. It has a figure eight cross-sectional shape 29, providing, along a principal axis, on a first common longitudinal centerline, a cylindrical-like body portion 36, called a short cap body cylinder 36, with an interior hollow cylindrical structure, designated as a needle protection cavity 21, to adequately receive a new needle 16, and also portions of the needle supported structure 22 of the syringe 15. Then this needle protection cavity 21 of this short cap 12 in this first cylindrical-like body portion 36, of this figure eight cross-sectional shape 29 has an interior hollow flaring portion, forming a flared receiving cavity 25, making a larger entry to the needle protection cavity 21. This flared receiving cavity 25 later receives portions of the bent needle 20.

Then another cylindrical-like body portion 37, called a short cap cavity cylinder 37, of the figure eight cross-sectional shape 29, arranged along a second common longitudinal centerline and located adjacent and parallel to the other cylindrical-like body portion 36, called the short cap body cylinder 36, of the figure eight cross-sectional shape 29, commences with a conical shaped cavity 18, serving as a needle bend gage, which is subsequently placed over the end portion of a needle bend length 19 of the hypodermic needle 16.

This conical shaped cavity structure, also referred to as a needle bend gage cavity, has a pocket depth, serving as a gage, to receive and to position a predetermined needle bend length 19 of the hypodermic needle 16, before this needle 16 is bent, when later this short cap assembly 2 is used as a tool to bend the needle end. In line, beyond the conical shaped cavity 18, there is a hollow cylindrical locating bore 33 later used to position a locating boss 34, on the second part called the short cover 14. This locating bore 33 is made longer to save plastic molding material and to keep the overall structure of this first part, called the short cap 12, of this shorter embodiment 2, both strong and easy to handle.

The second part, called the short cover 14, of this shorter embodiment 2, snugly overlaps the first part, such as at the shoulder location 35, where the interior hollow flaring portion, also called the cap receiving portion, is located. The interior of this second part, i.e. the short cover 14, has a syringe surrounding receiving chamber structure, called the cover receiving chamber 38, formed with a locking ring groove 24 and a locking ring-lip 23, which together, subsequently, also receive and capture the sharp end 17 of the bent needle 20, to in turn hold the entire short cap assembly 2 in place over the bent needle 20, during the disposal of the used hypodermic syringe 15. The follow on integral portions form a finger grip 30 of this second part 14, which also snugly surround the syringe 15. This second part, called the short cover 14, has a locating boss 34, which fits into the locating bore 33 of the short cap 12.

As shown in FIGS. 2, 4, 8, 9 and 10, this second part 14 is formed to include a surrounding finger guard flange 28. When a person is directing this shorter embodiment 2 of the multiple purpose protective hypodermic needle cap assembly 2, as a tool, over the sharp end 17 portion of the used hypodermic needle 16, this finger guard flange 28 insures the protection of the person's fingers, as he or she is using the short cap assembly 2, as a gage and as a tool to bend the sharp end 17 of the used hypodermic needle 16, into its non-use destroyed position. Then, subsequently, when this shorter embodiment of the multiple purpose protective hypodermic needle cap assembly 2 is directed over the bent needle 20, this finger guard flange 28 again serves to protect the fingers of the person, as he or she is moving this multiple purpose protective hypodermic needle cap assembly 2, over the entire bent hypodermic needle 20. At the completion of this protective capping movement, the sharp end 17 of the bent needle 20 enters the syringe surrounding receiving chamber 38 of the short cover 14, and is guided for entry into the receiving flared cavity 25 of the short cap 12. Thereafter, this sharp end 17 of the bent needle 20 is held, upon a one way latch action, by the predetermined needle bend length 19, which springs radially outwardly past the locking ring-lip 23, thereby causing the sharp end 17 of the bent needle 20 to engage the ring groove 24 of this second part 14, i.e. the short cover. The used syringe 15 is then ready for safe disposal.

Modified Multiple Purpose Protective Hypodermic Needle Cap Assemblies to Fit Two Piece Syringes Which Have Interchangeable Needles A modified multiple purpose protective hypodermic needle cap assembly 3, also called the internal grooved cap assembly 3, is shown in part in FIGS. 11 and 12. The changes made in contrast with the illustrated multiple purpose protective hypodermic needle cap assemblies 1 and 2, are made to accommodate two piece syringes 15, which have interchangeable needle retainers 39. These changes are applicable to both long cap and short cap assemblies, and they are illustrated in FIGS. 11 and 12 in respect to a long cap configuration.

As shown in FIGS. 11 and 12, either the long cap 11 or the short cap 12, are modified internally to have both internal locating ribs 40, which together provide the support structure 22 for supporting the interchangeable needle retainer 39, and axial grooves 41 to capture the bent needle 20, inclusive of the sharp end 17 of the needle. Also there is a needle clearance gap 42. Moreover there is a cap inner shoulder stop 31, which subsequently serves to contact the syringe end shoulder stop 32.

Also the long cover 13' and short cover 14' are slightly modified to have a larger entrance bore 26, to accept a flange 43 on the interchangeable needle retainer 39 of a two piece syringe. All the other respective functioning portions, i.e. features, of the long cap assembly 1 or the short cap assembly 2 of these multiple purpose protective hypodermic needle cap assemblies, as shown in FIGS. 1 through 10, remain the same. The same numerals for like parts are shown in FIGS. 11 and 12, for the parts shown in FIGS. 1 through 10.

The modified internal structures do not change the operation or function of this modified multiple purpose protective hypodermic needle cap assembly 3 in respect to the comparable operations and functions of long cap assembly 1 and short cap assembly 2.

The hypodermic needle 16 is bent by using a conical cavity 18. The modified cap assembly 1 or 2 is turned end for end and the bent needle 20, is pushed into the cover entrance bore 26. This forces the bent needle 20 through a clearance gap 42, until the sharp end 17 and the predetermined needle bend length 19, which has been bent, both together spring radially outwardly past the locking ring-lip 23 into an axial groove 41. Then the sharp end 17 of the bent needle 20 has been captured. Upon any attempted removal of a modified cap 11 or 12, the locking ring groove 24 interferes with such an attempt, as it continues to hold the sharp end 17 captive, and consequently the entire modified cap 11 or 12 is held captive, fully concealing the bent needle 20.

I claim:

1. A multiple purpose protective hypodermic needle cap, comprising a first part and a second part arranged longitudinally adjacent to one another a. the first part, called a cap, having the integral portions of:
      i. an interior hollow structure to receive a hypodermic needle and portions of a syringe;
      ii. an inner flared cavity structure to receive a bent hypodermic needle end and portions of a syringe and to contact the second part, and
      iii. a conical shaped cavity structure to serve as a hypodermic needle bend gauge; and
   b. the second part, called a cover, having the integral portions of:
      i. a syringe surrounding receiving chamber structure;
      ii. a receiving flared cavity structure, called a locking ring groove, to receive a bent hypodermic needle end, and a pointed sharp end thereof, and portions of a syringe and to contact the first part; and
      iii. an engagement circular lip structure, called a locking ring-lip, to receive and to capture in a one way latching motion, a pointed sharp end of a bent hypodermic needle end;

whereby this multiple purpose protective hypodermic needle cap is adapted to be used with a disposable hypodermic needle syringe: first, to protect a hypodermic needle during shipping and storing, until a syringe is ready for its medical use; second, after a syringe is utilized, the conical shaped cavity structure, which serves as a hypodermic needle bend gauge, is positioned over an end portion of a hypodermic needle, and then this multiple purpose protective hypodermic needle cap is used as a tool to bend back a pointed sharp end portion of a hypodermic needle beyond ninety degrees; third, the multiple purpose protective hypodermic needle cap is moved clear of a bent pointed sharp end portion of a hypodermic needle, then rotated and placed back over a bent pointed sharp end needle portion, and beyond; and fourth, the multiple purpose protective hypodermic needle cap is moved over a bent pointed sharp end needle portion, until a pointed sharp end of a bent pointed sharp end needle portion, radially expands, in a one way latching motion, into the receiving flared cavity structure and into a captured one way latching position with respect to the engagement circular lip structure, serving as a locking ring-lip, and thereafter a disposable hypodermic needle syringe, so covered by this multiple purpose protective hypodermic needle cap, is safely disposed of, for this protective hypodermic needle cap is locked on, and cannot be removed without completely destroying a hypodermic needle and/or a syringe.

2. A multiple purpose protective hypodermic needle cap, as claimed in claim 1, wherein in respect to the first part, called a cap, the conical shaped cavity structure to serve as a hypodermic needle bend gage, the interior hollow structure to receive a hypodermic needle and portions of a syringe, and the inner flared cavity structure are all aligned and arranged along a common longitudinal centerline, and wherein in respect to the second part, called a cover, the syringe surrounding receiving chamber structure, the receiving flared cavity structure to receive a bent hypodermic needle end, and the engagement circular lip structure, called a locking ring-lip, to receive and to capture, in a one way latching motion, a pointed sharp end of a bent hypodermic needle end, are all arranged along a common longitudinal centerline, which is in alignment with the common longitudinal centerline of the first part.

3. A multiple purpose protective hypodermic needle cap, as claimed in claim 1, wherein in respect to the first part, called a cover, the interior hollow structure to receive a hypodermic needle and portions of a syringe, and the inner flared cavity structure to receive a bent hypodermic needle end and portions of a syringe, are both arranged along a first common longitudinal centerline, and the conical shaped cavity structure to serve as a hypodermic needle bend gage is arranged along a second parallel longitudinal centerline and spaced adjacent the interior hollow structure, thereby shortening the length of the multiple purpose protective hypodermic needle cap, and wherein in respect to the second part, called a cover, the syringe surrounding receiving chamber structure, the receiving flared cavity structure to receive a bent hypodermic needle end, and the engagement circular lip structure, called a locking ring-lip, to receive and to capture, in a one way latching motion, a pointed sharp end of a bent hypodermic needle end are all arranged also along the extended first common longitudinal centerline of the first part.

4. A multiple purpose protective hypodermic needle cap, as claimed in claim 1, wherein the second part, called a cover, has, in addition, a surrounding finger guard flange, providing protection to a person's fingers, when she or he is manipulating the multiple purpose protective hypodermic needle cap, both when using it as a tool to bend a hypodermic needle and when using it to cover a hypodermic needle, initially when a needle is used and later when a needle has been bent and a one way latching motion occurs.

5. A multiple purpose protective hypodermic needle cap, as claimed in claim 2, wherein the second part, called a cover, has, in addition, a surrounding finger guard flange, providing protection to a person's fingers, when she or he is manipulating the multiple purpose protective hypodermic needle cap, both when using it as a tool to bend a hypodermic needle and when using it to cover a hypodermic needle, initially when a needle is used and later when a needle has been bent and a one way latching motion occurs.

6. A multiple purpose protective hypodermic needle cap, as claimed in claim 3, wherein the second part, called a cover, has, in addition, a surrounding finger guard flange, providing protection to a person's fingers, when she or he is manipulating the multiple purpose protective hypodermic needle cap, both when using it as a tool to bend a hypodermic needle and when using it to cover a hypodermic needle, initially when a needle is used and later when a needle has been bent and a one way latching motion occurs.

7. A multiple purpose protective hypodermic needle cap, as claimed in claim 1, wherein the second part, called a cover, has, in addition, a finger grip portion extending beyond the engagement circular lip structure.

8. A multiple purpose protective hypodermic needle cap, as claimed in claim 2, wherein the second part, called a cover, has, in addition, a finger grip portion extending beyond the engagement circular lip structure.

9. A multiple purpose protective hypodermic needle cap, as claimed in claim 3, wherein the second part, called a cover, has, in addition, a finger grip portion extending beyond the engagement circular lip structure.

10. A multiple purpose protective hypodermic needle cap, as claimed in claim 4, wherein the second part, called a cover, has, in addition, a finger grip portion extending beyond the engagement circular lip structure.

11. A multiple purpose protective hypodermic needle cap, as claimed in claim 5, wherein the second part, called a cover, has, in addition, a finger grip portion extending beyond the engagement circular lip structure.

12. A multiple purpose protective hypodermic needle cap, as claimed in claim 6, wherein the second part, called a cover, has, in addition, a finger grip portion extending beyond the engagement circular lip structure.

13. A multiple purpose protective hypodermic needle cap, as claimed in claim 3, wherein in respect to the first part, called a cap, in addition there is a hollow cylindrical structure also arranged along the second parallel longitudinal centerline beyond the conical shaped cavity structure and also spaced adjacent the interior hollow structure, which serves to align the cap with the cover, by serving as a locating bore, and to conserve plastic material during an injection molding process, and yet continues to provide strength to this first part; and wherein, in respect to the second part, called a cover, in addition, there is a locating boss which, upon assembly of the first part and the second part, enters the locating bore of the hollow cylindrical structure of the first part, both insuring the alignment of the cap and cover, and helping to connect the first part to the second part.

14. A multiple purpose protective hypodermic needle cap, as claimed in claim 13, wherein in respect to the first part, called a cap, the outside appears as a figure eight in respect to the end view thereof, and thereby materials are conserved while strength is provided.

15. A multiple purpose protective hypodermic needle cap, as claimed in claim 1, wherein the first part and the second part, when made of plastic, are joined together utilizing a method optionally employing adhesives, heat, or ultrasonic welding.

16. A multiple purpose protective hypodermic needle cap, as claimed in claim 1, wherein the interior hollow structure of the first part, called the cap receiving cavity, has both axial spaced locating ribs adapted to position a portion of the length of a hypodermic needle syringe, and respective adjacent axial spaced grooves, with each of the grooves adapted to receive a bent needle end.

17. A multiple purpose protective hypodermic needle cap, as claimed in claim 16, wherein the syringe surrounding receiving structure of the second part accommodates a flange of a two piece syringe provided with an interchangeable needle retainer and a needle.

* * * * *